United States Patent [19]
Baratta

[11] Patent Number: 5,813,982
[45] Date of Patent: Sep. 29, 1998

[54] NONCONTACTING PORTABLE INFRARED INTRA-OCULAR PRESSURE SENSOR

[76] Inventor: Francis I. Baratta, 138 Ridge St., Arlington, Mass. 02174-1737

[21] Appl. No.: 199,636

[22] Filed: Feb. 22, 1994

[51] Int. Cl.⁶ .................................. A61B 3/16; A61B 6/00
[52] U.S. Cl. ............................ 600/398; 600/474; 600/549
[58] Field of Search ....................... 128/645–52, 897–98, 128/736, 664; 364/557; 374/100, 120, 121, 129, 130, 131; 600/398–406, 549, 473–477

[56] References Cited

U.S. PATENT DOCUMENTS

| | | | |
|---|---|---|---|
| 4,626,686 | 12/1986 | Pompei et al. | 374/128 |
| 4,797,840 | 1/1989 | Fraden | 128/736 |
| 5,199,436 | 4/1993 | Pompei et al. | 128/736 |

OTHER PUBLICATIONS

Disclosure No. 303164, Mar. 1992, Baratta.
*Gray's Anatomy, 35th British Edition,* eds. R. Warwick and P.L. williams, Publisher W.B. Saunders, Co., 1973, Philadelphia, PA, p. 1105.
L.M. Parver, et al., "Choriodal Blood Flow as a Heat dissipation Mechanism in the Macula", Journal of Ophthalmology, vol. 89, 1989, p. 643.
L.M. Parver, "Temperature Modulating Action of Choriodal Blood Flow," Eye, vol. 5, 1991, p. 182.
*The American Medical Association Encyclopedia of Medicine,* ed. Charles B. Clayman, Random House, 1989, New York, NY, p. 489.
J.M. Looney Jr., and F. Pompei, "Ear Thermometry," Medical Electronics, 1989, p. 1.

*Primary Examiner*—John P. Lacyk
*Attorney, Agent, or Firm*—Jeffrey D. Marshall

[57] ABSTRACT

Medical studies have shown that when the pressure within the eye rises above normal the flow of blood is suppressed to the veins and the optic nerve fibers causing a reduction of temperature at those locations. If such conditions are allowed to exist over a period of time the subject is in danger of experiencing loss of peripheral vision, called glaucoma.

This invention presents an improved way to determine indirectly intra-ocular pressure of the human eye through the use of a noncontacting, nonirrating, infrared temperature sensing device. This is accomplished by accurately measuring the temperature at the macula and fovea sites located at the back of the eye and the core body temperature as the individual's base temperature using the same tympanic temperature measuring device. The difference in these temperatures, calibrated in terms of intra-ocular pressure, reveals the potential danger of impending glaucoma. The read-out can easily be put in terms of a threshold warning to the user as a visual and/or audible warning signal. The device can be employed as an accurate tonometer to replace the presently used mechanical tonometers, or as a screening test.

20 Claims, 2 Drawing Sheets

NONCONTACTING PORTABLE INFRARED INTRA-OCULAR PRESSURE SENSOR

FIELD OF INVENTION

This invention relates to the detection of intra-ocular pressure by a comparison of the core body temperature, defined by a tympanic membrane measurement, to an intra-ocular temperature measurement with the differential between each of these measurements yielding an accurate indirect measure of intra-ocular pressure.

SUMMARY OF INVENTION

Intra-ocular pressure (IOP) above the normal average pressure suppresses blood flow to the veins and optic nerve fibers at the back of the eye, and if sustained long enough above a prescribed threshold level can result in glaucoma. This constriction of blood flow results in a decrease in the retinal-choroidal temperature. A major physiological role of the choriod is to help maintain a stable temperature environment for the retina; if high IOP exists that role is suppressed. The present invention relates to the indirect measurement of IOP using an infrared (IR) sensor by accurately measuring the temperature of the macula; a small central area containing a pit, called the fovea, located near the posterior pole of the eye. Core body temperature measurement is readily obtained at the tympanic membrane using the current state-of-the-art ear thermometry device. Appropriate circuitry is provided to effect the difference between the temperature at the macula and the accurately measured core body temperature, used as a base for reference. This difference is easily calibrated in terms of the intra-ocular pressure (IOP) existing in the vitreous humor of the interior chamber of the eye. A negative difference greater than a predetermined magnitude gives a warning of impending glaucoma, which in turn can be programmed as a visual and/or audible read-out warning signal to the user. The device can be employed as an accurate tonometer to replace the presently used mechanical tonometers, or as a screening technique.

BACKGROUND OF THE INVENTION AND PRIOR ART

Glaucoma causes blindness for 15 percent of blind adults in the United States and of those over age 40 nearly 2 percent have chronic glaucoma, according to *The American Medical Association Encyclopedia of Medicine*, ed. Charles B. Clayman, Random House, New York, N.Y., 1989. About 10 percent of people over 70 years of age have excessive pressure within their eyes. Glaucoma is a condition that when the pressure of the fluid within the eye is above the average pressure, can cause deadening of the optic nerve fibers. The average intra-ocular pressure (IOP) for most individuals is about 15 mm to 20 mm of mercury (Hg) above atmospheric pressure. This damage occurs because of constriction of blood flow to the internal blood vessels and/or the optic nerve fibers. The resulting fiber destruction can cause permanent loss of peripheral vision, which is not apparent to the affected person until the latter stages of severe irreversible damage. This condition if left untreated can result in permanent blindness. The Intra-ocular pressure above the average level can be reduced and controlled in most patients by surgery or by medication taken either internally or applied externally to the affected eyes. Surgical procedures can subsequently cause visual problems, and long term dosage of currently available drugs can eventually result in undesirable side effects.

Intra-ocular pressure above the threshold level that causes permanent damage (approximately 30 mm of Hg), compresses and restricts the flow of blood in the internal blood vessels at the back of the eye. Medical studies performed on the eyes of cynomolgus monkeys (the eye anatomy of these animals are very similar to those of humans) have shown that a reduction of the retinal-choroidal temperature, in particular at the macula as a function of the increase in IOP, is greater than 0.5° C. for an increase of from 15 to 30 mm Hg of pressure, see "Choriodal Blood Flow as a Heat Dissipating Mechanism in the Macula", by L. M. Parver, et al., American Journal of Ophthalmology, Vol. 89, 1990, and "Temperature Modulating Action of Choroidal Blood", by L. M. Parver, Eye, Vol. 5, 1991. However, the present day IR sensors with their electronic instrumentation, which are used to measure body core temperature via the tympanic membrane, are accurate to within 0.10° C., see "Ear Thermometry", by J. M. Looney, JR., and F. Pompei, Medical Electronics, 1989, and U.S. Pat. No. 5,199,436, a tympanic measurement device wherein it is claimed to measure the core body temperature to 0.10° C. over a wide range of ambient temperatures.

GLAUCOMA DETECTION

At present glaucoma is detected by regular routine eye examinations by trained medical personnel. Those suffering from, or susceptible to glaucoma require frequent inconvenient visits to an ophthalmologist for time consuming and expensive examinations. The subject's eyes are first locally anesthetized and then the IOP is measured by a tonometer, an instrument available to the ophthalmologist that measures the force to flatten a predetermined small area of the eyeball. This force, previously calibrated by experimentation, is related to the flattened area, resulting in a pressure read-out. The surface area of the eye is mechanically displaced by either a flat contacting anvil or a sudden puff of air. Both of these methods can cause considerable discomfort to the subject. These problems associated with the mechanical measurement of intra-ocular pressure (IOP) have not been met. Thus, there is a need for a convenient, low cost, portable, noncontacting tonometer for those persons having chronic or congenital glaucoma and for those having sensitive eyes. Such a system would allow a medical professional or a lay person to measure IOP without applying local anesthesia and without physically contacting the eyes.

As stated above the state-of-the-art tympanic temperature measurement device, such as that described in U.S. Pat. No. 5,199,436, is adopted here for use to measure both the core body temperature as a base of reference and the temperature at the back of the eye. In addition, a detachable eye piece assembly incorporating a Fresnel lens is slightly force-fitted into the distal end of the ear measurement device. This assembly is used for both stand-off, so that the device does not contact the patient's eyes during use and to reduce the field of view so that the beam diameter is less than that of the pupil of the eye.

TEMPERATURE DETECTION

Temperature measurement is important because if it is above normal it indicates to the physician that the body is fighting an infection or disease, etc. Acceptable clinical methods measure core body temperature under the tongue or in the rectum, and consist of utilizing a thermal probe, such as a mercury thermometer, or an electronic display device using a thermocouple or a thermistor. The basic problem not met by all three of these devices is that they measure their own temperature; not the temperature of the subject. Utilization of these instruments requires intimate contact for a sufficient length of time to raise their temperature to nearly that of the patient. Also, when attempting to determine sublingual temperature these devices will yield inaccurate readings by at least several degrees, if they are not properly located under the tongue. Further, if these instruments are not left in place long enough to equilibrate; incorrect readings will result. The behavior of the subject will also affect the accuracy of these devices, such as: breathing, speaking, movement of the probe from under the tongue, smoking and consumption of hot or cold liquids.

DESCRIPTION OF THE INVENTION

This invention meets the need for a noncontacting, nonirritating, portable tonometer to monitor the intra-ocular pressure in the eye for those patients who are susceptible to glaucoma and whose eyes are sensitive to local anesthesia and/or physical contact by the presently used tonometers.

This proposed method measures the internal temperature at the back of the eye and compares it to the subject's core temperature. A negative temperature difference related to intra-ocular pressure difference greater than a predetermined threshold value can indicate the onset of glaucoma. Thus, this system will allow a patient to monitor his/her own IOP on a daily basis, if required. In this way the time between medical visits could be extended.

Additionally, if the pressure level rises above the threshold level that cause loss of peripheral vision, the device acting as a screening test would a give warning, and the patient could immediately seek medical aid.

The presently proposed invention incorporates an infrared sensor that measures the difference between the temperature at the back of the eye and the temperature of the tympanic membrane, which represents the core body temperature as a base for reference. This temperature difference is related to the pressure difference, since the increase in IOP is known as a function of decreased temperature of the macula.

Tympanic temperature measurements are readily obtained from the present state-of-the-art commercially available devices. They utilize the output of a thermopile and support electronics that respond to sensed radiation. The housing of such devices incorporates a disposable conical speculum that is inserted into the ear canal for measurement of the tympanic temperature. An eye piece for stand-off can be incorporated to hold a Fresnel lens, as described in U.S. Pat. No. 4,626,686, and also mentioned in U.S. Pat. No. 4,797,840, to reduce the field of view of the IR detector in the tympanic measurement instrument so that the beam diameter is less than that of the pupil of the eye. Note that pupil diameters can range from 1 mm to 8 mm in size, See *Gray's Anatomy*, 35*th British Edition*, eds. R. Warwick and P. L. Williams, W. B. Saunders Co., Philadelphia, 1973. According to the former patent such a device can be matched to the lens of the IR sensor so as to provide the same original flux density independent of the field of view.

The eye piece can be made of the same material as the disposable speculum used in practice, e.g., a polyethylene polymer, but of a dark hue so that the pupil of the eye will not contract. Alternatively, the pupils can be dilated if required. Note that the other eye should be closed or covered and preferably the test conducted in subdued light such that the pupils of both eyes will not contract. This will allow the full field of view of the IR beam to be transmitted through the pupil and lens system of the eye to the macula area. Corrective glasses and contact lenses are to be retained and the patient is to stare directly into the device so as to focus the IR beam on the macula and foveal areas. These areas are particularly sensitive to temperature as a function of pressure, and if the pressure is above normal it can result in decreased temperature. However, care must be taken that the eyes are not exposed to bright background light, else the light-generated thermal load in the macula produced by the focussing of the eye's optical system will cause an increase in the IOP, see "Choriodal Blood Flow as a Heat dissipation Mechanism in the Macula", Parver et al., American Journal of Ophthalmology, Vol. 89, 1980. Barring such an occurrence, the temperature differences measured by the Noncontacting Portable Infrared Intra-ocular Pressure Sensor, related to pressure differences above a prescribed threshold level, will reveal the possibility of the onset of glaucoma. The device will initiate a visual and/or audible warning signal to the user when his/her individual threshold level is exceeded. The invention can be used as a replacement to the to the mechanical tonometers presently in use, or as a home portable screening aid.

BRIEF DESCRIPTION OF DRAWINGS

The foregoing and other objects, features and advantages of the invention will be apparent from the following more particular description of preferred embodiments of the invention, as illustrated in the accompanying drawings. The drawings are not necessarily to scale, emphasis instead being placed upon illustrating the principles of the invention.

PREFERRED EMBODIMENT

An infrared device, such as that described in U.S. Pat. No. 5,199,436, is first employed to obtain a body core temperature signal by inserting in the ear canal a tympanic temperature detector and then focusing it on to the back of the eye to obtain a temperature signal from the macula. The electronic signals are programmed by the device to either provide an intra-ocular pressure read-out or give an audible/visual warning signal. A subsequent discussion provides the details of the electronic circuitry and the mathematical process.

As previously mentioned, the temperature of the macula is directly related and sensitive to the change in intra-ocular pressure; the difference between the subject's core temperature and his/her eye temperature will reveal intra-ocular pressure. If this pressure difference is greater than a predetermined level then glaucoma can occur.

Figure 1:
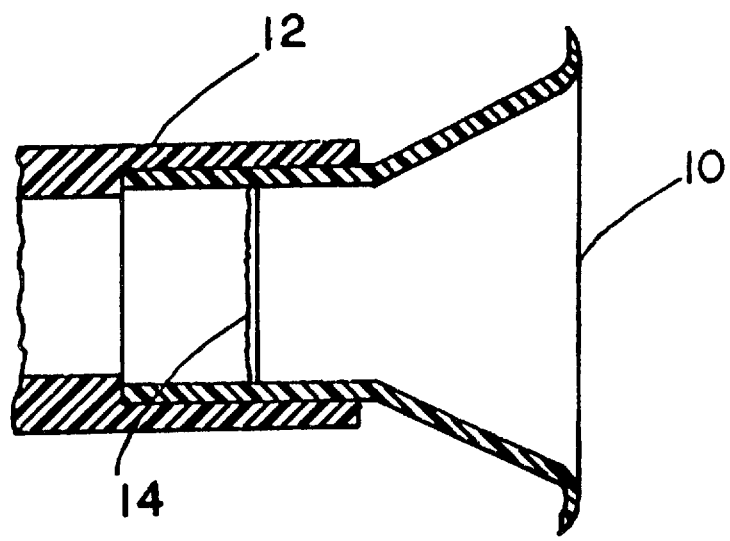
FIG. 1 is a cross-sectional view of the eye piece and Fresnel lens assembly.

FIG. 1 shows the eye piece assembly 10 held in the distal end of the tympanic temperature detector 12 by a light interference fit and the Fresnel lens 14 within the barrel of the eye piece assembly. The eye piece assembly is used as a stand-off so that the instrument would not inadvertently be poked in the eye. A Fresnel Lens 14 is employed to reduce the field of view of the IR detector in the tympanic temperature measurement instrument so that the beam diameter is less than that of the pupil of the eye. Yet, the assembly is designed to still provide the original flux density independent of the field of view, see U.S. Pat. No. 4,626,686.

When the tympanic temperature detector is inserted in the ear canal a disposable conical speculum is placed over the distal end of the unit for sanitary reasons. Since this a standard design for such devices, it is neither shown nor discussed here. However, again referring to FIG. 1, which shows the eye piece assembly 10, a disposable conical speculum can easily be adapted to be the same outside diameter of this assembly, such that it also fits snugly into the bore of the temperature detector 12.

The temperature sensing device can readily be designed so as to be portable or attached on a track which is mounted on 'the unit', as it is commonly called. This unit, an articulated frame housing various ophthalmoscopic instruments is used to locate and focus said instruments into the patient's eyes by the ophthalmologist. The temperature sensing device, mounted to the unit, such that, as previously described, is first located and inserted within the patient's ear to measure the tympanic temperature and then rotated approximately 90 degrees and focused into the eye to measure the macula temperature.

Figure 2:
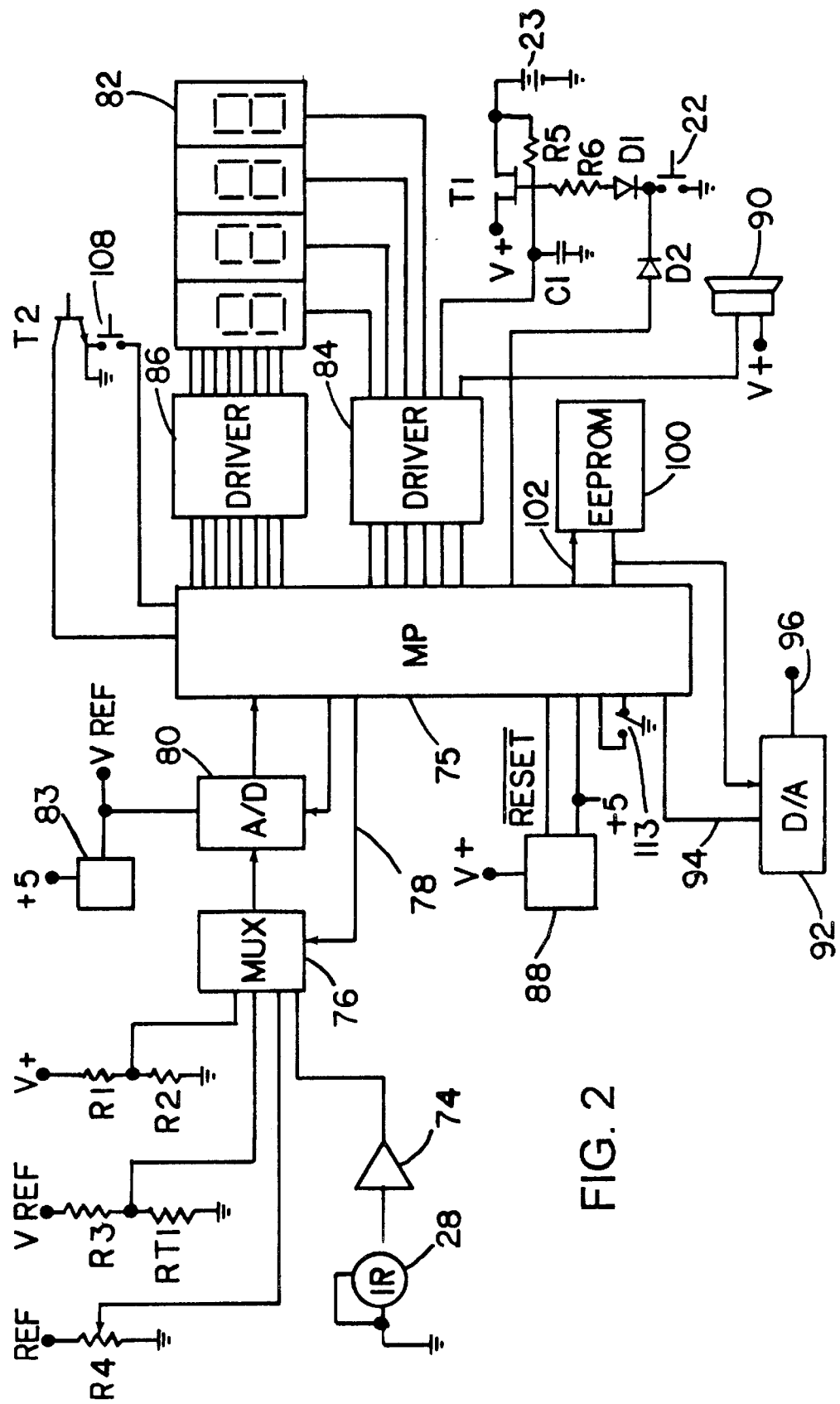
FIG. 2 is a block diagram of the electronic circuit of the detector.

A schematic of the electronics is illustration in FIG. 2 of the infrared temperature detector. The circuitry is the same as that of U.S. Pat. No. 5,199,436, except the microprocessor is programmed such that sequence of events are different than that of the referred patent. This will subsequently be described. The detector provides a readout on display 82 in response to the signal from the thermopile 28. The system is based on a microprocessor 75, which processes software routines included in read only memory within the processor chip. The processor may be a 6805 processor sold by Motorola. The voltage generated across the thermopile 28 due to a temperature differential between the hot and cold junctions is amplified in an operational amplifier 74. The analog output from the amplifier 74 is applied as one input to the multiplexer 76. Another input to the multiplexer 76 is a voltage taken from a voltage divider R1, R2 which is indicative of the potential V+ from the power supply 23. A third input to the multiplexer 76 is the potential across the thermistor RT1 mounted in the bore of the unit (refer to FIG. 2 of U.S. Pat. No. 5,199,436). The thermistor RT1 is coupled in a voltage divider circuit with R3 across a reference potential VRef. The final input to the multiplexer is a potential taken from the potentiometer R4, which may be adjusted by the user. The system may be programmed to respond to that input in many ways. In particular, the potentiometer may be used as a gain control or as a DC offset control. At any time during the software routine of the microprocessor 75, one of the four inputs may be selected by the select lines 78. The selected analog signal is applied to a multiple slope analog system 80, used by the microprocessor in an integral analog-to-digital conversion 80. The subsystem 80 may be a TSC500A sold by Teledyne. It utilizes the reference voltage VRef from a reference source 83. The microprocessor 75 responds to the output from the convertor 80 to generate a count indicative of the analog input to the convertor.

The microprocessor drives four 7-segmented LED displays 82 in a multiplexed fashion. Individual displays are selected sequentially through a column driver 84, and within each selected display the seven segments are controlled through segment driver 86.

When switch 22 is pressed by the user, it closes the circuit from the battery 23 through the resistors R5 and R6; and diode D1 to ground. The capacitor C1 is quickly charged and the field effect transistor T1 is turned on. Through transistor T1 and the V+potential from the storage cell 23 is applied to a voltage regulator 88, which provides the regulated +5 volts to the system. It also provides a reset signal to the microprocessor. The reset signal is low until the +5 volt reference is available and thus holds the microprocessor in a reset state. When the +5 volts is available, the reset signal goes high, and the microprocessor begins its programmed routine.

When the switch 22 is released, it opens its circuit, but a charge is maintained on capacitor C1 to keep transistor T1 on. Thus, the system continues to operate. However, the capacitor C1 and transistor T1 provide a very simple watchdog circuit. Periodically, the microprocessor applies a signal through driver 84 to the capacitor C1 to recharge the capacitor and thus keep the transistor T1 on. If the microprocessor should fail to continue in its programmed routine, it fails to charge the capacitor C1 within a predetermined time during which the charge on C1 leaks to a level at which transistor T1 turns off. Thus, the microprocessor must continue on its programmed routine or the system shuts down. This prevents spurious readings when the processor is not operating property.

With transistor T1 on, the switch 22 can be used as an input through diode D2 to the microprocessor to initiate any programmed action of the processor.

In addition to the display, the system has a sound output 90, which is driven through the driver 84 by the microprocessor.

In order to provide an analog output from the detector, a digital-to-analog convertor 92 is provided. When selected by line 94, the convertor converts serial data on line 96 to an analog output made available to the user.

Both calibration and characterization data required for processing by the microprocessor may be stored in the electrically erasable programmable read only memory (EEPROM) 100. The EEPROM may, for example, be a 93c46 sold by CMOS Technologies, Inc. The data may be stored in the EEPROM by the microprocessor when the EEPROM is selected by line 102. Once stored in the EEPROM, the data is retained even after power down. Thus, though electrically programmable, once programmed the EEPROM serves as a virtually nonvolatile memory.

Prior to shipment, the EEPROM may be programmed through the microprocessor to store calibration data for calibrating the thermistor and thermopile. Further, characterization data which defines the personality of the of the infrared detector may be stored. For example, the same electronics hardware, including the microprocessor 75 with its internal program, may be used for a tympanic temperature detector and a macula temperature detector in which the output is accurate in the target temperature of about 60 degrees F. to 110 degrees F., or it may be used as an industrial detector in which the target temperature range would be from 0 degrees F. to 100 degrees F. Further, different modes of operation may be programmed into the system. For example several different uses of the sound source 90 are available.

Proper calibration of the detector is readily determined and the EEPROM is readily programmed by means of an optical communication link which includes a transistor T2 associated with the display 82. A communication boot may be placed over the read-out end of the detector during the calibration/characterization procedure. A photodiod in the boot generates a digitally encoded optical signal which is filtered and applied to the detector T2 to provide an input to the microprocessor 75. In a reverse direction, the microprocessor may communicate optically to a detector in the boot by flashing specific segments of the digital display 82. Through that communication link, an outside computer can monitor the outputs from the thermistor and the thermopile and perform a calibration of the devices. A unit to be calibrated is pointed at each of two black body radiation sources while the microprocessor 75 converts the signals and sends the values to the external computer. The computer is provided with the actual black body temperatures and ambient temperature in the controlled environment of the detector, and computes calibration variables and returns those variables to be stored in the EEPROM. Similarly, data which characterizes a particular radiation detector may be communicated to the microprocessor for storage in the EEPROM.

A switch 113 may be provided either internally or through the housing to the user to set a mode of operation of the detector. By positioning the switch at either the lock position, the scan position, or a neutral position; any three of the modes may be selected. The first mode is the normal scan mode where the display is updated continuously. A second mode is a lock mode where the display locks after a selectable delay and then remains frozen until the power is cycled or, optionally, the power-on button is pushed. The sound source may be caused to sound at the time of the lock. The third mode is the peak mode where the display reads the maximum value found since power-on is initiated until power is cycled or, optionally, the power-on button is pushed.

The processor determines when the voltage from the divider R1, R2 drops below each of the two thresholds. Below the higher threshold, the processor periodically enables the sound source to indicate that the battery is low and should be replaced, but allows continuous readings from the display. Below the lower threshold, the processor determines that any output would be unreliable and no longer displays temperature readings. The unit would then shut down upon release of the power button.

The present system utilizes the same state-of-the-art computations as that of U.S. Pat. No. 5,199,436, regarding: the target temperature (Tt), the gain calibration factor (Kh), the hot junction temperature (Vi), the Seebeck coefficient (Atav), and the actual sensor output (Vs). Because these formulae are fully discussed in the above named patent they are not presented or discussed here.

To determine the temperature, the microprocessor makes several computations: First the signal from the thermistor RT1 is converted to temperature using a linear approximation.

The temperature is represented by a set of linear equations, such as $$T = M(x - xo) + b \quad (1)$$

where M is the slope of a straight line approximation, x is an input and xo is an input end point. The values of M, xo and b are stored in the EEPROM after calibration. Thus, to obtain temperature from the thermistor, the microprocessor determines from the values of xo, the line segment in which the temperature fall: and then performs the computation for T based on the variables M and b stored in the EEPROM.

Secondly, the hot junction temperature is computed. A fourth power representation of the hot junction temperature is then obtained by a look up table in the processor ROM.

Thirdly, the sensed radiation may be corrected using the gain calibration factor Kh, the sensor gain temperature coefficient Tco, the average of the hot and cold junction temperatures and a calibration temperature Tz is stored in the EEPROM. The corrected radiation signal and the fourth power of the hot junction temperature are summed and the fourth root is taken. The fourth root calculation is also based on a linear approximation which is selected according to the temperature range of interest for a particular unit. Again, the break points and coefficients for each linear approximation are stored in the EEPROM and are selected as required.

As in U.S. Pat. No. 5,199,436, there is an additional factor based on ambient temperature which also has to be included as an adjustment. The temperature of the ear Te and that of the eye Ti, which are sensed by the thermopile, are neither the core temperature nor the eye temperature. There is a thermal resistance between the core temperature Tcr and Te, as well as a thermal resistance between the macula temperature Tm and the eye temperature Ti. Further, there is a thermal resistance between the sensed ear temperature and ambient temperature, and similarly there is a thermal resistance between the sensed eye temperature and ambient temperature. Thus the sense temperature Te is a function of the core temperature and ambient temperature. Accordingly, the sense temperature Ti is a function of the macula temperature and the ambient temperature. Therefore, these temperatures, Tcr and Tm, are shown calculated in the paragraphs that follow.

The core temperature can be computed as $$Tcr = Ta + (Ti - Ta)/Kce \quad (2)$$

The above is based on an assumed constant Kce, which is a measure of the thermal resistance between Tcr, Te and Ta.

Similarly, the macula temperature can be computed as $$Tm = Ta + (Ti - Ta)/Kci \quad (3)$$

And as before, the above is based on an assumed constant Kci, which is a measure of the thermal resistance between Tm, Ti and Ta.

These computations can account for a difference of from one-half to one degree between the objectively desired temperatures and the sensed temperatures, depending on ambient temperature.

A similar computation can be made in other applications. For example, in difference cutaneous temperature scanning, the significance of a given differential reading may be ambient temperature dependent.

According to Parver and Parver et al.,(see "Temperature Modulating Action of Blood Flow", L. M. Parver; and "Choroidal Blood Flow as a Heat dissipating Mechanism in the Macula," L. M. Parver et al.) there is a direct linear relationship between the retinal-choriodal temperature and the intra-ocular pressure from approximately 99.4 degrees F. to 97.6 degrees F. The difference between the core temperature Tcr and the macula temperature Tm represents the difference in intra-ocular pressure above the normal value, i.e., the temperature decreases as the IOP increases. Therefore, delta Pm of the macula is simply, where Mm is the slope of the straight line relationship $$\text{delta } Pm = Mm(Tcr - Tm) \quad (4)$$

If delta Pm is above a certain value, then damage to the optic nerve endings can occur.

The microprocessor may be readily programmed such that when the unit is placed in the ear canal and switch 23 is first pressed, the temperature Te will be sensed and Tcr will be determined according to equations 1 and 2; then the microprocessor will store and hold that data. While the unit is aimed at the eye, as previously described, and switch 23 is activated the second time, the temperature Ti will be sensed and Tm will be calculated according to equations 1 and 3; then the processor will determine delta Pm according to equation 4. A read-out will be displayed on 82 for the use of the medical profession. Pressing switch 23 the third time removes the display and allows the unit to be ready for the next sequence of measurements. For home use a sound system may be operational. If delta Pm is above a prescribed level that may cause glaucoma a continuous warning will sound (via 90) until the user presses switch 23 the third time shutting off the sound; then the unit is ready for the next sequence of measurements. If delta Pm is at a normal level a series of continuous beeps will be heard until the sound is shut off after switch 23 is again activated and the unit ready for reuse. So as to conserve battery power if switch 23 is not activated for the third time the unit will shut down after a reasonable interval.

Since U.S. Pat. No. 5,199,436 has shown in detail the required steps to program the microprocessor and the EEPROM, it is not necessary to repeat here either those steps or the additional ones indicated in the above paragraph.

I claim:

1. A method to detect relative inter-ocular pressure where: a first sensor is directed at the tympanic membrane within one ear of a patient, and where said first sensor generates a first signal proportional to a core temperature of said patient; and where a first signal processing means converts said first signal into a core output signal, and where a second detector is directed at the macula of one eye of said patient by a directing means; and where said second sensor generates a second signal proportional to the temperature of said patient's macula, and where a second signal processing means converts said second signal into a macula output signal, and where said core output signal and said macula output signal are compared by a primary comparing means, and where an output from said means is further compared with a preset value by a secondary comparison means, and where when the output exceeds preset values an alarm processing means provides audible, visible, tactile, electronic, or printed warning indicators.

2. The method in 1 where a further focusing apparatus is inserted in the optical path between the eye and the second sensor, and where an adjustable or fixed focal distance is maintained by a housing holding said focusing apparatus and said second sensor.

3. The method in 2 where said focusing apparatus is a Fresnel lens.

4. The method in 1 where a single sensor is used in place of said first and second sensor, said single rotatable sensor mounted by rotatable mounting means to sense tympanic and macular temperature in series.

5. The method in 4 where said rotatable means is a two position holder said single sensor.

6. The method in 4 where said rotatable mounting means is attached to the unit which houses ophthalmoscopic instruments and which guides, and enables focusing of said single sensor.

7. The method in 1 where a further analog or digital reading of comparative temperatures is provided.

8. The method in 1 where a further processing comparator means follows said comparison means and said processing comparator means compares said signed proportional signal to an oppositely signed reference signal, and where if said signal has a signed magnitude signal indicating said reference signal is larger (smaller) than said signed proportional signal, then said signed magnitude signal is directed to said output processing means.

9. The claim of 1 where said dual sensors are infrared sensors.

10. The claim of 9 where said infrared sensors are directed for said first sensor at the tympanic membrane and for said second sensor at the macula of the eye.

11. The method in 4 where said single sensor is an infrared sensor.

12. The method in 11 where said infrared sensor is directed at the tympanic membrane and for said sensor at the macula of the eye.

13. A process to identify high intra-ocular pressure where, dual sensors are provided, the first sensor directed at an area of the body by first directing means, which can produce a first signal directly related to a body core temperature, and a second sensor directed through the pupil of an eye by a second directed means to produce a second output signal directly relatable to the macula temperature of the eye, and where a comparison means input results of said first signal and said second signal output signal and produces a signed signal proportional to the difference magnitude between said first signal and said second signed output signal, and where said signal proportional signal is processed by output processing means by display means to produce a readout which is relatable to intra-ocular pressure.

14. The process in 13 where said directed means is a focusing lens within a housing which is adjustable while touching at least one reference point on the head.

15. The process in 14 where said focusing means is a Fresnel lens.

16. The process in 14 where said focusing means is incorporated within the unit that also contains ophthalmoscopic instruments and which includes reference scales and focusing means.

17. The process in 13 where a single sensor is employed which is serially locatable for measuring both tympanic temperature and macular temperature.

18. The process in 17 where a storage device stores the temperature information from said tympanic and said macular temperature prior to said comparison means and which provides input to said comparison means.

19. A device lo measure macular temperature and compare it to the tympanic temperature where a sensor detects the tympanic temperature and this temperature value is electronically or manually inputted to a comparison means which takes a signal from an infrared sensor viewing the temperature of the macula of the eye through a focused lens, and where said comparison means provides a differential output indicating the signed variance between the tympanic and macular temperatures.

20. The device in 19 where said focused lens is a Fresnel lens.

* * * * *